United States Patent [19]

Kratz

[11] Patent Number: 4,623,796
[45] Date of Patent: Nov. 18, 1986

[54] TANNING APPARATUS WITH MEANS WHICH AID FACIAL TANNING

[76] Inventor: Walter Kratz, Auf der Heide 21, D-5208 Eitorf, Fed. Rep. of Germany

[21] Appl. No.: 720,728

[22] Filed: Apr. 8, 1985

[30] Foreign Application Priority Data

Apr. 11, 1984 [DE] Fed. Rep. of Germany ....... 3413662

[51] Int. Cl.$^4$ .............................................. A61N 5/06
[52] U.S. Cl. ............................ 250/504 R; 250/494.1; 250/492.1; 250/454.1
[58] Field of Search ............ 250/504 R, 493.1, 494.1, 250/453.1, 454.1, 455.1, 492.1; 128/372

[56] References Cited

U.S. PATENT DOCUMENTS 4,177,834 12/1979 Wolff ................................. 250/504
4,196,354 4/1980 Wolff ................................. 250/504

Primary Examiner—Bruce C. Anderson
Assistant Examiner—Jack I. Berman
Attorney, Agent, or Firm—Fleit, Jacobson, Cohn & Price

[57] ABSTRACT

Tanning apparatus with means which assist facial tanning and low pressure tubes irradiating in the UV-A spectral range, said tubes being arranged in a plate which is at least transparent for UV-A rays in a lower part shaped in the form of a bed and/or in a downwardly radiating upper part of the browning apparatus over the entire longitudinal extension thereof, a reflector being provided on the side of the low pressure tubes remote from the tanning body, wherein the means aiding facial tanning in the region of the tanning apparatus where the face to be tanned is located comprises further low pressure tubes over and beyond the low pressure tubes extending over the length of the tanning apparatus.

16 Claims, 3 Drawing Figures

TANNING APPARATUS WITH MEANS WHICH AID FACIAL TANNING

BACKGROUND OF THE INVENTION

The present invention relates to a tanning apparatus with means which assist facial tanning and low pressure tubes irradiating in the UV-A spectral range, said tubes being arranged in a plate which is at least transparent for UV-A rays in a lower part shaped in the form of a bed and/or in a downwardly radiating upper part of the browning apparatus over the entire longitudinal extension thereof, a reflector being provided on the side of the low pressure tubes remote from the tanning body.

Nowadays such tanning apparatuses preferably use so-called UV-A rays, i.e. the longest wave rays in the ultraviolet range following on to the visible spectrum. In the skin, these rays convert colourless pigment precursors into brown melanin.

As the skin of the face is generally much more frequently exposed to solar radiation than the remainder of the skin of the body, in many persons the face tans much more slowly than the rest of the body, even in the case of uniform radiation action. However, as many users of tanning apparatuses attach particular importance to the tanning of the face, high power burners are provided in the facial region in conventional tanning apparatuses. The radiation source is then constituted by a metal-halogen UV-A burner. However, such a burner produces UV-B rays, as well as the desired UV-A rays and although the former activates the regeneration of colourless pigment granules, they cause sunburn in the case of excessive intensity. Thus, considerable amounts of UV-B radiation must be filtered out when using such conventional metal—halogen burners in the facial area and for this purpose expensive filter plates must be used.

A further disadvantage of conventional metal—halogen burners is that, in the case of high power consumption, they are also subject to heating and heat the surrounding components of the tanning apparatus through the emission of IR-radiation, so that both the burner and the surrounding components must be very effectively cooled. IR-radiation also leads to a considerable heating effect on the face of the tanning person, and is considered unpleasant by the latter. The conventional metal—halogen burners can also only produce with difficulty a large, uniform radiation field.

SUMMARY OF THE INVENTION

The problem of the present invention is therefore to so further develop the browning apparatus defined hereinbefore, that the additional means for aiding the tanning of the face only produce limited infrared radiation, has a large, uniform radiation field and requires no additional filter plate. In addition, it is intended that the special means for aiding facial tanning should be subsequently installable in older tanning apparatuses with low pressure tubes, without an independent reflector being necessary. The facial tanning means requires no special cooling device.

According to the invention this problem is solved in that the means aiding facial tanning in the region of the tanning apparatus where the face to be tanned is located comprises further low pressure tubes over and beyond the low pressure tubes extending over the length of the tanning apparatus.

Preferably the additional low pressure tubes for facial tanning are located in the upper part of the tanning apparatus, but it is also conceivable to arrange said additional low pressure tubes in the lower part of the apparatus.

According to an advantageous further development of the invention, the additional low pressure tubes are arranged in such a way that they are positioned between the low pressure tubes extending along the tanning apparatus and the plate which is transparent to UV-A radiation. The additional low pressure tubes are positioned above the gaps present between the low pressure tubes extending along the tanning apparatus, so that the radiation of both types of low pressure tubes reaches the body or face in an unimpeded manner.

According to a further development of the invention, the additional low pressure tubes are mounted on a separate e.g. acrylic glass plate, which can be placed on a recess in the plate covering the low pressure tubes extending along the tanning apparatus, in such a way that the additional low pressure tubes project into the cavity between the reflector and the plate. This in particular permits a subsequent installation of the means for aiding facial tanning according to the invention in conventional equipment. The plate provided with the additional low pressure tubes is preferably fixed by means of screws to the plate covering the low pressure tubes extending along the tanning apparatus, so that the additional low pressure tubes can be easily replaced if faults occur.

A particularly simple cooling of the area with the additional low pressure tubes can be achieved in that openings are provided in the plate having the additional low pressure tubes for the circulation of cooling air.

BRIEF DESCRIPTION OF THE DRAWINGS

The invention is described in greater detail hereinafter relative to a non-limitative embodiment and the attached drawings, wherein show.

DETAILED DESCRIPTION OF THE INVENTION

Figure 1:
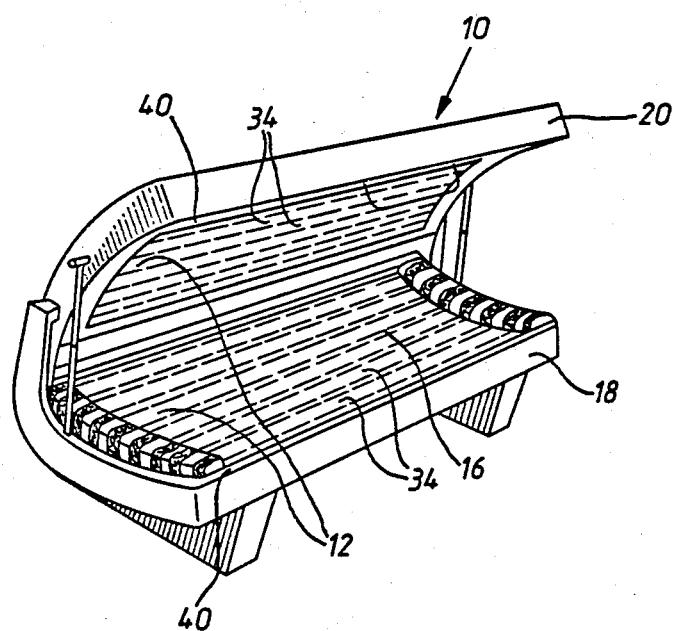
FIG. 1 a perspective view of a conventional tanning apparatus, in which the means for aiding facial tanning according to the invention can be used.

The tanning apparatus 10 shown in FIG. 1 has a lower part 18 shaped in the manner of a bed and an upper part 20 articulated thereto. Low pressure tubes 34 are arranged with parallel longitudinal axes over the length of the bed in upper part 20 and lower part 18. Above the low pressure tubes 34 is provided an acrylic glass plate 16, which is transparent to UV-rays. Thus, the tanning person lies on the plate 16 of lower part 18 and is consequently irradiated by the low pressure tubes 34 both in lower part 18 and in upper part 20. The head part of the tanning person is consequently located in area 12 of the tanning apparatus 10.

Figure 2:
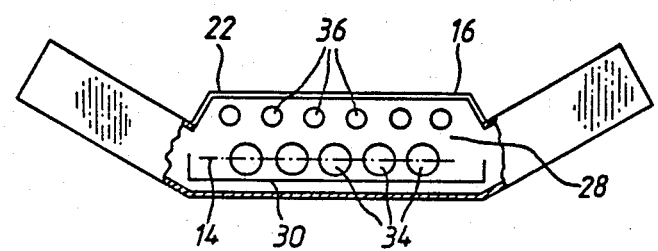
FIG. 2 a section through a tanning apparatus in which the means for aiding facial tanning according to the invention is used.

FIG. 2 shows a section through a tanning apparatus 10 in the area of the face to be tanned. The low pressure tubes 34 extend roughly over the entire length of lower part 18 and/or upper part 10 and are used for the general tanning of the body. A reflector 30 is arranged on the side of the low pressure tubes 34 remote from the body to be tanned. The axes of the elongated low pressure tubes 34 are located in one plane 14. The additional low pressure tubes 36 are arranged in the cavity 28 between the plane 14 defined by the low pressure tubes 34 and the acrylic glass plate 16.

Figure 3:
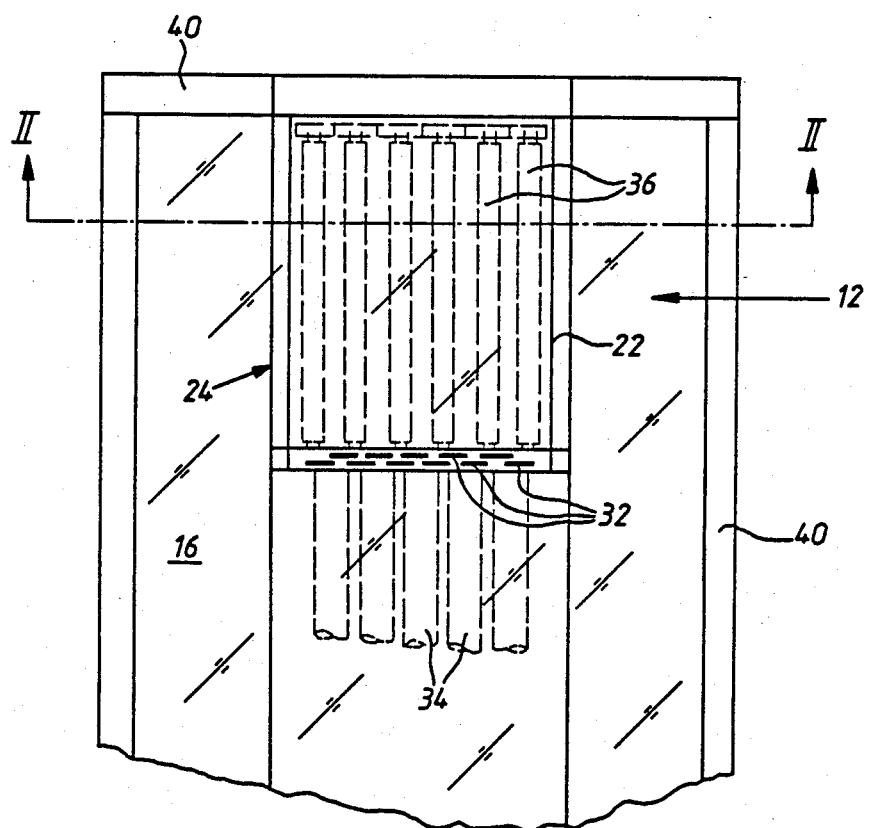
FIG. 3 a plan view of a detail of the upper part of a tanning apparatus with the means for aiding facial tanning according to invention.

FIG. 3 is a plan view of the area 12 of lower part 18 or upper part 20 of tanning apparatus 10, which is shown in FIG. 2 in section along line II—II. Acrylic glass plate 16 is secured in frame 14. The low pressure tubes 34 extending over roughly the entire length of the tanning apparatus 10 are located below the acrylic glass plate 16. In area 12, a recess 24 is provided in the acrylic glass plate 16 and into it are introduced the additional low pressure tubes 36 used for facial tanning purposes. The additional low pressure tubes 36, and their sockets and starters are mounted on an acrylic glass plate 22, whose dimensions correspond to recess 24 and is fixed there e.g. by means of screws. Acrylic glass plate 22 has slot-like holes 32, through which by means of a not shown blower, air currents for cooling the additional low pressure tubes 36 pass into the cavity 28. Four to twelve additional low pressure tubes 36 may be provided. According to FIGS. 2 and 3, the additional low pressure tubes 36 are staggered with respect to the low pressure tubes 34 extending over the length of the tanning apparatus 10, i.e. the radiation of the elongated low pressure tubes and the radiation reflected by reflector 30 passes unimpeded through the gaps between the additional low pressure tubes 36. The diameter of the latter is in this embodiment 26 mm. The power consumption of each additional low pressure tube 36 is between 30 and 40 watt, for a length of approximately 44 cm. It is contemplated that the length of the elongated low pressure tubes 34 could be 180 cm, the length of the additional low pressure tubes 36 could be between 44 and 60 cm, and the power consumption of the additional low pressure tubes could be between 30 and 65 watts.

It is obvious that the means according to the invention for aiding facial tanning can also be used in tanning apparatuses comprising either the bed only, or the upper part irradiating the lying person from above.

The inventive features disclosed by the description, claims and drawings can be essential, either individually or in random combination, for the realization of the invention.

What is claimed is:

1. A tanning apparatus with means which assist facial tanning and low pressure tubes irradiating in the UV-A spectral range, said tubes being arranged in a plate which is at least transparent for UV-A rays in a lower part shaped in the form of a bed and/or in a downwardly radiating upper part of the tanning apparatus over the entire longitudinal extension thereof, a reflector being provided on the side of the low pressure tubes remote from the tanning body, wherein the means aiding facial tanning in the region of the tanning apparatus where the face to be tanned is located comprises further low pressure tubes over and beyond the low pressure tubes extending over the length of the tanning apparatus.

2. A tanning apparatus according to claim 1, wherein the additional low pressure tubes are positioned between the low pressure tubes extending along the tanning apparatus and the plate which is transparent to UV-A rays.

3. A tanning apparatus according to claim 1, wherein the additional low pressure tubes are provided in the lower part of the tanning apparatus.

4. A tanning apparatus according to claim 1, wherein the additional low pressure tubes are provided in the upper part of the tanning apparatus.

5. A tanning apparatus according to claim 1, wherein the additional low pressure tubes are provided both in the lower part and in the upper part of the tanning apparatus.

6. A tanning apparatus according to claim 1, wherein the additional low pressure tubes are staggered with respect to the low pressure tubes extending along the tanning apparatus.

7. A tanning apparatus according to claim 1, wherein four to twelve additional low pressure tubes are provided.

8. A tanning apparatus according to claim 1, wherein the additional low pressure tubes in each case have a power consumption of 30 to 65 watt.

9. A tanning apparatus according to claim 1, wherein the additional low pressure tubes have in each case a diameter of 26 mm.

10. A tanning apparatus according to claim 1, wherein the additional low pressure tubes have in each case a length of 44 to 60 cm.

11. A tanning apparatus according to claim 1, wherein the low pressure tubes extending along the tanning apparatus have a length of 180 cm.

12. A tanning apparatus according to claim 1, wherein six additional low pressure tubes are provided in the lower part and/or upper part, in addition to the low pressure tubes extending along the tanning apparatus.

13. A tanning apparatus according to claim 1, wherein the additional low pressure tubes are mounted on an acrylic glass plate, which can be placed on a recess in the plate covering the low pressure tubes extending along the tanning apparatus, in such a way that the additional low pressure tubes project into the cavity between the reflector and the two plates.

14. A tanning apparatus according to claim 13, wherein on the plate provided with the additional low pressure tubes are fixed sockets and/or starters for said additional low pressure tubes.

15. A tanning apparatus according to claim 13, wherein recesses for the circulation of cooling air are provided in the plate having the additional low pressure tubes.

16. A tanning apparatus according to claim 13, wherein the plate provided with the additional low pressure tubes is fixed by means of screws to the plate covering the low pressure tubes extending along the tanning apparatus.

* * * * *